United States Patent [19]

Cregan et al.

[11] Patent Number: 5,229,114
[45] Date of Patent: Jul. 20, 1993

[54] APPROACHES USEFUL FOR THE CONTROL OF ROOT NODULATION OF LEGUMINOUS PLANTS

[75] Inventors: Perry B. Cregan, Jessup; Harold H. Keyser, Clarksville; Michael J. Sadowsky, Columbia, all of Md.

[73] Assignee: The United States of America as represented by the Secretary of Agriculture, Washington, D.C.

[21] Appl. No.: 87,356

[22] Filed: Aug. 20, 1987

[51] Int. Cl.$^5$ ............... A01N 63/00; C12R 1/41; A01C 1/06; A01H 1/00; C05F 11/08
[52] U.S. Cl. ............... 424/93 D; 435/252.2; 435/878; 47/57.6; 47/58; 71/7
[58] Field of Search ............... 424/93, 93 D; 47/58, 47/57.6, 57, 605, 58.09; 71/7; 435/252.2, 878

[56] References Cited

PUBLICATIONS

Cregan et al. 1986 Crop Science 26(5):911–916.
Devine et al. 1980. Can. J. Microbiol. 26(2): 179–182.
Vest et al. 1972, Crop Science 12:692–693.
Devine et al. 1977, Euphytica 26: 527–535.
V. G. Reyes et al., "Population Densities of *Rhizobium japonicum* Strain 123 Estimated Directly in Soil and Rhizospheres," Appl. Environ. Microbial, 37: 854–858 (1979).
E. P. Dunigan et al., "Introduction and Survival of an Inoculant Strain of *Rhizobium japonicum* in Soil," Agron. J. 76: 463–466 (1984).
G. E. Ham, "Competition Among Strains of Rhizobia," World Soybean Res. Interstate Printers & Publishers, L. D. Hill (ed) pp. 144–150 (1976).
W. R. Ellis et al., "Persistence and Recovery of *Rhizobium japonicum* Inoculum in a Field Soil," Agron. J. 76: 573–576 (1984).

*Primary Examiner*—David T. Fox
*Attorney, Agent, or Firm*—M. Howard Silverstein

[57] ABSTRACT

A novel approach for the increased dinitrogen fixation of leguminous plants wherein the root nodulation of the leguminous plant is controlled so as to promote nodulation by a desired bradyrhizobial strain and to inhibit nodulation of an undesired bradyrhizobial strain. Novel leguminous plant lines are provided which restrict nodulation by undesired bradyrhizobial strains while allowing nodulation of a desired bradyrhizobial strain. The plant lines are produced by conventional breeding. Recombinant bradyrhizobial strains are also provided which are characterized by a propensity for root nodulation of a predetermined leguminous plant. The recombinant bradyrhizobial strains are produced by genetic engineering.

1 Claim, No Drawings

APPROACHES USEFUL FOR THE CONTROL OF ROOT NODULATION OF LEGUMINOUS PLANTS

BACKGROUND OF THE INVENTION

1. Field of the Invention

This invention pertains to novel methods and vehicles for the increased dinitrogen fixation of leguminous plants. More specifically, the present invention relates to novel leguminous plant lines, recombinant root nodulating bacteria, and the method of use thereof to control the root nodulation and dinitrogen fixation of leguminous plants.

2. Description of the Prior Art

A major emphasis of recent research in the field of $N_2$ fixation has been the development and application of bradyrhizobial strains with enhanced $N_2$ fixation. However, establishing an introduced strain of Bradyrhizobium japonicum "*B. japonicum*" in the nodules of soybean [*Glycine max* (L.) Merr.] grown in soils populated by indigenous bradyrhizobia has been, and remains, a critical problem.

Most soils of the United States where a soybean crop has been grown have an indigenous population of the homologous root nodule bacterium, *B. japonicum*. These indigenous bradyrhizobia are usually excellent competitors for nodulation of soybean in comparison with applied inoculant strains. In the major soybean growing areas of the midwest, the most competitive population of *B. japonicum* is that of serogroup 123. If improvement in the dinitrogen fixing capacity of the soybean-Bradyrhizobium symbiosis through application of superior strains is to be realized, then the difficult problem of competition from indigenous populations (such as serogroup 123) will have to be solved.

Significant efforts have been made to understand and alter the competitiveness of indigenous bradyrhizobia. For example, attempts to alter soybean nodule occupancy ratios of indigenous versus applied bradyrhizobia have been reported. However, such alterations were only achieved by using ultra-high, economically infeasible rates of the applied strain. In a seven year study, E. P. Dunigan et al. [Agron. J. 76: 463–466 (1984)] demonstrated that the inoculant strain USDA 110 eventually formed the majority of nodules after high rates of application in the first 2 years (serogroup 123 was not among the indigenous population). However, the tenacious competitive ability of serogroup 123 appears not to be related to numbers per se and when normal rates of inoculum are applied the indigenous serogroup 123 population can still form up to 95% of the nodules on soybean.

SUMMARY OF THE INVENTION

We have now developed a novel approach for the control of dinitrogen fixation of leguminous plants which solves the problem presented by the competitiveness of indigenous bradyrhizobial strains. In the method of the invention, the host leguminous plant serves as the vehicle to restrict nodulation by an indigenous and/or undesired bradyrhizobia while allowing nodulation of a more desired bradyrhizobial strain which is capable of a more effective dinitrogen fixation. Our approach is economical and highly effective for the enhancement of leguminous plant productivity.

Accordingly, it is an object of the present invention to provide an economical method for the increased nitrogen fixation of leguminous plants which overcomes problems associated with the competitiveness of indigenous bradyrhizobial strains.

It is also an object of the invention to provide a method for the selective restriction of the nodulation of leguminous plants by predetermined bradyrhizobial strains wherein the host leguminous plant serves as the vehicle for restriction.

Still, another object of the present invention is to provide a novel leguminous plant line capable of restricting nodulation of undesired bradyrhizobial strains in favor of a desired bradyrhizobial strain.

It is also another object of the present invention to provide recombinant bradyrhizobial strains having a propensity for the nodulation of a predetermined plant line.

DETAILED DESCRIPTION OF THE INVENTION

In accordance with the method of the invention, the host leguminous plant serves as the vehicle to restrict nodulation by an indigenous or undesired bradyrhizobia while allowing nodulation of a more desired bradyrhizobial strain which is capable of a more effective dinitrogen fixation. In general, the selective nodulation of the host leguminous plant is accomplished by a method comprising the steps of (1) identifying the nodulation genes for each desired bradyrhizobial strain; (2) providing a leguminous plant having at least one nodulation inhibitor gene which does not have a corresponding nodulation gene in each of said indigenous or undesired bradyrhizobial strain; and (3) growing said leguminous plant in the presence of a desired bradyrhizobial strain wherein said desired bradyrhizobial strain is characterized by a genotype having a nodulation gene corresponding to each nodulation inhibitor gene in said plant.

The leguminous plant useful in the method of the invention is any leguminous plant, such as soybeans, cowpeas and the like, which is capable of restricting the nodulation of undesired bradyrhizobial strains. The leguminous plants are characterized by a genotype which (1) restricts nodulation by undesired bradyrhizobial strains, wherein said genotype has at least one nodulation inhibitor gene which does not have a corresponding nodulation gene in said undesired bradyrhizobial strain; and (2) permits nodulation of desired bradyrhizobial strains such that nodulation genes are provided in said desired bradyrhizobial strain which correspond to each nodulation inhibitor gene in the plant.

Preferably, the leguminous plants used in the invention are from leguminous plant lines which have been established by conventional breeding using the steps of (1) identifying in a variety of leguminous plants nodulation inhibitor genes which do not have a corresponding nodulation gene in undesired bradyrhizobial strains; and (2) combining said nodulation inhibitor genes in the genome of a single leguminous plant genotype. As will be obvious to one skilled in the arts, the novel genotypes of the invention may have the capability to restrict nodulation of one or more bradyrhizobial strains.

The desired bradyrhizobial strain useful in the invention is any bradyrhizobial strain which is capable of enhanced dinitrogen fixation through root nodulation of leguminous plants and which is characterized by a genotype having a nodulation gene corresponding to each nodulation inhibitor gene in the plant.

Preferably, the desired bradyrhizobial strain is a recombinant bradyrhizobial strain characterized by a propensity for root nodulation of predetermined leguminous plants, wherein the bradyrhizobial strain is provided with nodulation genes which correspond to each nodulation inhibitor gene in a predetermined leguminous plant. The recombinant bradyrhizobial strain is established by genetic engineering using the steps of (a) identifying in a variety of desired bradyrhizobial strains nodulation genes which correspond to at least one nodulation inhibitor gene in a predetermined leguminous plant; and (b) providing said nodulation genes into a single bradyrhizobial strain. The recombinant bradyrhizobial strains may be genetically engineered to effectively nodulate a single leguminous plant having a single nodulation inhibitor gene, a variety of leguminous plants having a variety of nodulation inhibitor genes or a single leguminous plant having a multiplicity of nodulation inhibitor genes.

The method of the invention is useful to restrict root nodulation of a predetermined leguminous plant by any undesired bradyrhizobial strain, in particular the highly competitive bacteria of *B. japonicum* serogroup 123, while simultaneously permitting nodulation of a desired bradyrhizobial strain. However, as will be obvious to those skilled in the arts, the concept of the invention also encompasses the selective nodulation of a leguminous plant by other root nodulating bacteria, such as other rhizobial strains.

The following is intended to further illustrate the invention and not to limit the scope of the invention as defined by the claims.

EXAMPLE 1

One or more soybean genotypes that restricted nodulation by *B. japonicum* strain USDA 123 were identified and tested for their capacity to preferentially nodulate with an inoculation strain other than strain USDA 123.

MATERIALS AND METHODS

Initial Screening Experiments

Samples of all the available accessions in the USDA soybean germplasm collection of Maturity Groups VI through X were obtained courtesy of Dr. E. E. Hartwig (USDA-ARS, Stoneville, MS 38776). In an initial experiment, seeds of 720 Maturity Group VI and VIII accessions, which included 679 plant introductions and 41 cultivars, were screened for their ability to nodulate with *B. japonicum* strain USDA 123. An autoclaved mixture of equal volumes of vermiculite and coarse perlite was placed in 25 cm plastic pots that had been soaked overnight in a sterilizing solution of 800 $\mu$L L$^{-1}$ Rocal II$^3$ (Dimethyl benzyl ammonium chloride) (National Laboratories, Montvale, N.J.) followed by rinsing in tap water. Seeds of each accession were surface sterilized by immersion in acidified HgCl$_2$ for 2 min followed by five rinses in distilled water. Six different accessions were planted in separate hills at a depth of 2 cm in each pot using six seeds of each accession per hill. Before covering, each hill was inoculated with 2 ml of stationary broth culture (approximately 10$^9$ cells ml$^{-1}$) of strain USDA 123. Eight additional pots were planted with six hills each of the soybean cultivar 'Lee'. Seeds in two of these pots were inoculated with USDA 123, two pots were inoculated with strain USDA 110, and the four remaining pots were left uninoculated. After covering the seeds, the vermiculite-perlite medium was covered with a 1 cm layer of sterile coarse perlite to serve as a dry barrier to prevent contamination by extraneous *B. japonicum*. Seedlings were thinned to two per hill at 4 days after emergence. At 2 weeks after planting, all pots received 500 ml of N-free nutrient solution. At 19 and 26 days after seeding, two of the uninoculated pots containing Lee soybean were given 15 ml of a 0.4M Ca(NO$_3$)$_2$ solution. These latter pots served as the N control treatment. Plants were grown in the greenhouse with natural sunlight supplemented by incandescent light to extend the photoperiod to 18 h. Day and night temperatures were maintained at 25±5° C. At 42 days after seeding, the plants were washed and examined. The nodulation of each root system was visually assessed by comparison with the nodulated root system of soybean cultivar Lee. In those accessions in which nodule number was obviously less than Lee, the number of nodules per root was determined. Accessions with less than 10 nodules (or that had germinated or grown poorly) were rescreened in the same manner as described above in order to confirm the nodule response obtained in the initial screening.

In a subsequent experiment, germplasm accessions from Maturity Groups VIII through X, which included 24 cultivars and 534 plant introductions, were seeded, inoculated, and otherwise treated and evaluated as described above. Again, those accessions with less than 10 nodules or that had germinated or grown poorly were rescreened.

Secondary Screening

Those accessions that appeared to have restricted nodulation with USDA 123 based upon the initial screening and rescreening tests described above were evaluated in a subsequent experiment using Monmouth fine sandy loam soil (Alfic Normudult) for the University of Maryland Tobacco Farm at Upper Marlboro, Md. This soil had no detectable *B. japonicum* ($<10$ cells g$^{-1}$ soil) as determined by a most probable number (MPN) test using the plant infection method. The soil was limed to a neutral pH and placed in 25 cm plastic pots that had been sterilized with Rocal II as described above. Seeds were surface sterilized and groups of five germplasm accessions were planted in each of two duplicate pots using hills of five seeds for each accession. In addition, a sixth hill in each pot was planted with the soybean cultivar 'Bragg'. Before covering, the seeds in one of the two duplicate pots were inoculated as described above with strain USDA 123 and the other duplicate pot was inoculated in a similar manner with an equal mixture of strains USDA 6, USDA 110, and USDA 136. Three additional pots were each planted with the soybean cultivars Bragg, 'Williams', 'Corsoy', 'Hodgson', Lee and 'Essex'. Seeds in one pot were inoculated with strain USDA 123, while the seeds in the second were inoculated with a mixture of USDA 6, USDA 110, and USDA 136. The third pot served as an uninoculated control. After plant, the soil surface was covered with a 1 cm layer of sterile gravel. Greenhouse photoperiod and temperature conditions were similar to those described above. Plants were thinned to two per hill. At 34 days after seeding the plants were removed from the soil and the number of nodules per root system was determined.

Two germplasm accessions that had demonstrated particularly limited nodulation with strain USDA 123 in the initial screening were examined in two separate experiments to obtain quantitative estimates of nodulation and $N_2$ fixation with strain USDA 123 in relation to *B. japonicum* strains normally considered to be highly effective. These experiments included:

Experiment 1. A randomized complete block with four replications was employed in which each replication consisted of one 25 cm plastic pot sterilized as described above and filled with autoclaved vermiculite. Each pot was planted with one hill each of PI 371607, PI 377578, and Essex (a standard check cultivar) using five surface-sterilized seeds per hill. Before covering, the seeds were inoculated with *B. japonicum* strain USDA 123 as described above. After planting, the vermiculite surface was covered with a 1 cm layer of sterile coarse perlite. Nitrogen-free nutrient solution was applied as described above and greenhouse conditions were similar to those described previously. At 30 days after seeding, plants were harvested and the nodules removed, dried, and weighed. The plant tops above the cotyledonary node were removed and dried for subsequent determination of N content of duplicate samples using an Erba Nitrogen Analyser[3] (Carlo Erba Strumentazione, Milan, Italy).

Experiment 2. A randomized complete block design with four replications was used. The treatments consisted of a factorial arrangement of two soybean genotypes and three inoculation treatments. Leonard jar assemblies L. T. Leonard [J. Bacteriol. 45: 523-527 (1943)] were filled with vermiculite, autoclaved, and planted with one hill of five surface sterilized seeds of either PI 371607 or PI 377578. Before covering, the seeds were either inoculated with 2 ml of stationary broth culture of strain USDA 123; 2 ml of a mixture of strains USDA 6, USDA 110, and USDA 122; or were left uninoculated. The experiment was conducted in a growth chamber with an 18-h photoperiod, 25° C. day temperature, 20° C. night temperature, and a photon flux density of $392\mu$ mol $m^{-2}s^{-1}$ at seedling level. At 40 days after seeding, the plants were harvested and treated as described in Exp. 1.

Rhizobial Competition for Nodulation

Experiment 3. A randomized complete block experimental design was used that consisted of a split plot arrangement of treatments and four replications. Whole plots (pots) were inoculation treatments and subplots were soybean genotypes. Soybean-rhizobia-free Monmouth soil (5.2 kg pot$^{-1}$) was preinoculated with strain USDA 123 by alternately spraying and mixing the soil with a culture dilution prepared from a 5-day yeast-mannitol-salts medium. A determination of viable cells showed that $1.4 \times 10^6$ cells were added $g^{-1}$ soil. Each pot was then planted with two hills each of PI 371607, PI 377578, and cultivar Williams. Three competition treatments were developed by inoculating each hill of each pot with 1 ml of 6-day yeast-mannitol-broth culture containing 9.3, 3.4, or $4.0 \times 10^6$ cells of either USDA 110, USDA 122, or USDA 138, respectively. In this manner three treatments were established to allow a determination of the competition for nodulation between USDA 123 and USDA 110, USDA 123 and USDA 122, and USDA 123 and USDA 138. After covering the seed, 1 cm layer of sterile gravel was placed upon the soil surface. Seedlings were thinned to one per hill. Greenhouse conditions were similar to those described above. At 28 days after planting, the plants were harvested nd the nodules removed. The nodules from the two plants of each genotype within each pot were combined and oven dried. The serogroup of the strain occupying 15 nodules from each replication of each soybean genotype-competition treatment combination was determined using strain specific fluorescent antibodies as described by E. L. Schmidt et al. [J. Bacteriol. 95: 1987-1992 (1968)]. Fluorescent antibodies of strains USDA 123 and USDA 110, USDA 123 and USDA 122, or USDA 123 and USDA 138 were used depending upon the competition treatment being analyzed.

Experiment 4. The experimental design was similar to that of Exp. 3. The inoculation treatments (whole plots) consisted of (1) an uninoculated control; (2) preinoculation with strain USDA 123 to a level of $1.8 \times 10^6$ cells $g^{-1}$ soil; (3) preinoculation with strain USDA 110 to a level of $4.9 \times 10^6$ cells $g^{-1}$ soil; and (4) preinoculation with strain USDA 123 followed by seed inoculation using a yeast-mannitol-broth culture ($1.7 \times 10^9$ cells hill$^{-1}$) of USDA 110 at planting. Treatment 4 was established to allow a determination of competition for nodulation between strains USDA 123 and USDA 110. Preinoculation was performed in the same manner as described for Exp. 3. The subplots were the genotypes PI 371607, PI 377578, and Williams planted as described for Exp. 3. At 42 days after planting, the plants were harvested and the nodules removed, dried, and weighed. The plant tops above the cotyledonary node were excised and dried for subsequent N analysis of duplicate samples using the Erba Nitrogen Analyser[3]. The nodules and plant tops from the two plants of each genotype within each pot were combined. The strain present in 30 nodules per replication of each soybean genotype receiving Treatment 4 was determined using strain specific fluorescent antibodies of both USDA 123 and USDA 110.

RESULTS

Initial Screening Experiments

The initial screening of germplasm accessions of Maturity Groups VI through X identified 22 genotypes with restricted nodulation when grown in artificial medium and inoculated with strain USDA 123. The selected genotypes produced from one to as many as eight nodules per plant. In contrast, the cultivar Lee consistently produced 30 or more nodules as did most of the germplasm accessions. In some instances when germination or growth was poor, the accessions were poorly nodulated as compared to Lee and other genotypes with vigorous healthy growth. The uninoculated control of cultivar Lee provided a basis for discrimination between poor growth resulting from N starvation and that resulting from other factors relating to poor vigor or disease. Thus, the 22 genotypes that were selected demonstrated healthy vigorous growth as well as restricted nodulation with strain USDA 123. Other accessions included in our screening may also restrict nodulation by strain USDA 123, but did not, in our judgement, grow adequately well to allow us to clearly distinguish between restricted nodulation and poor growth.

Secondary Screening Experiments

This experiment examined the nodulation response of the 22 genotypes that were identified in the initial screening experiments. All of the control genotypes produced greater than 30 nodules with USDA 123 (Table I). Nine of the 22 test genotypes produced more than 5 nodules, whereas 13 accessions had two or less nodules per plant. In general, we noted that nodulation with strain USDA 123 on these 13 genotypes were more restricted in the B. japonicum-free soil than we had observed previously in the vermiculite-perlite mixture. When inoculated with a mixture of B. japonicum strains USDA 6, USDA 110, and USDA 136 these 13 accessions nodulated at least as well as the control cultivars. The 13 genotypes selected included at least one representative from each of the five maturity groups and included cultivars as well as plant introductions.

Experiments 1 and 2. Of the 13 USDA 123 restricting genotypes, PI 371607 and PI 377578 were chosen for further testing because sufficient seeds were available.

TABLE I

Number of nodules produced on soybean cultivars and plant introductions inoculated with Bradyrhizobium japonicum strain USDA 123 and a mixture of strains USDA 6, USDA 110, and USDA 136 (Secondary screening)

| Soybean genotype | Maturity group | Mean nodule no. With USDA 123 | Mean nodule no. With mixture of USDA 6, 110, 136 | Nodulation phenotype |
|---|---|---|---|---|
| | | nodules plant$^{-1}$ | | |
| Bragg | VII | >30 | >30 | N |
| Williams | III | >30 | >30 | N |
| Corsoy | II | >30 | >30 | N |
| Hodgson | I | >30 | >30 | N |
| Lee | VI | >30 | >30 | N |
| Essex | V | >30 | >30 | N |
| PI 371607 | VI | 1 | >30 | R |
| PI 376844 | VII | 2 | >30 | R |
| PI 377578 | VII | 0.5 | >30 | R |
| Acadian | VIII | 0 | >30 | R |
| Arisoy | VIII | 0 | >30 | R |
| Improved Pelican | VIII | 1 | >30 | R |
| White Biloxi | VIII | 1 | >30 | R |
| PI 263044 | VIII | 1 | >30 | R |
| PI 445842 | VIII | 0 | >30 | R |
| PI 324187 | IX | 0 | >30 | R |
| PI 325779 | IX | 2 | >30 | R |
| PI 341248 | IX | 0 | >30 | R |
| PI 163308 | X | 0.5 | >30 | R |

Values are the mean of two plants.
N = normal nodulation with strain USDA 123, and R = restricted nodulation with strain USDA 123.

When compared to the cultivar Essex, PI 371607 and PI 377578 nodulated to a limited extent (Table II). Similarly, the N accumulation of the PI genotypes was significantly less than that of cultivar Essex. The nodule dry weight of PI 371607 and PI 377578, when inoculated with strain USDA 123, was significantly less than that obtained with a mixture of strains USDA 6, USDA 110, and USDA 122 (Table III). When inoculated with strain USDA 123, the N accumulation of the two PI genotypes was not significantly different from the uninoculated control and was less than one-third of that obtained with the mixture of strains. These results supported our preliminary finding that nodulation by strain USDA 123 is restricted in PI 371607 and PI 377578.

Rhizobial Competition for Nodulation

The development of a genotype that restricted nodulation by strain USDA 123 would be of little use unless a corresponding increase in nodulation by strains of other more desirable serogroups was obtained. Thus, two experiments were conducted to test the effect of two genotypes restricting nodulation by strain USDA 123 in a situation in which both strain USDA 123 and a strain of another serogroup were present simultaneously in the rhizosphere.

Experiment 3. Monmouth soil containing no detectable B. japonicum was preinoculated to obtain approximately 10$^6$ cells of strain USDA 123 throughout the 25 cm pot in an effort to simulate the background strain USDA 123 population of a northern midwestern U.S. soil. Both PI 371607 and PI 377578 preferentially nodulated with either USDA 110, USDA 122, or USDA 138 rather than strain USDA 123, when compared to the commonly grown cultivar Williams (Table IV). The difference in the proportion of nodules occupied by strain USDA 123 in the PI genotypes vs. Williams was substantial. Across the three rhizobial competition treatments, a mean of 80% of the Williams nodules contained strain USDA 123 in contrast to a mean of only 4% of the nodules of the PI genotypes. The inoculant strain appeared in 97% or more of the nodules of the PI genotypes but never exceeded 44% in Williams.

TABLE II

Nodulation and N accumulation of PI 371607, PI 377578, and Essex grown in vermiculite and inoculated with Bradyrhizobium japonicum strain USDA 123 (Exp. 1)

| Genotype | Nodule dry wt | Nitrogen accumulation |
|---|---|---|
| | mg plant$^{-1}$ | |
| PI 371607 | 4b | 5b |
| PI 377578 | 5b | 5b |
| Essex | 34a | 17a |

Values are the mean of four plants.
Values within a column not followed by the same letter differ significantly at the 0.05 probability level as tested by Duncan's new multiple range test.

TABLE III

Nodulation and N accumulation of PI 371607 and PI 377578 grown in vermiculite and inoculated with Bradyrhizobium japonicum strain USDA 123 or a mixture of strains USDA 6, USDA 110 and USDA 122 (Exp. 2)

| Rhizobium treatment | Nodule dry wt PI 371607 | Nodule dry wt PI 377578 | Nitrogen accumulation PI 371607 | Nitrogen accumulation PI 377578 |
|---|---|---|---|---|
| | mg plant$^{-1}$ | | | |
| Uninoculated | 0c | 0b | 3b | 3b |
| USDA 123 | 120b | 42b | 9b | 7b |
| USDA 6 + 110 + 122 | 185a | 207a | 29a | 28a |

Values are the mean of four plants.
Values within a column not followed by the same letter differ significantly at the 0.05 probability level as tested by Duncan's new multiple range test.

TABLE IV

Strains recovered from the nodules of PI 371607, PI 377578, and Williams in three nodulation competition treatments established by preinoculation of Monmouth soil with strain USDA 123 followed by inoculation with either strains USDA 110, USDA 122, or USDA 138 at planting (Exp. 3)

| Soybean genotype | Nodulation competition treatment USDA 123 vs. USDA 110 | | | USDA 123 vs. USDA 122 | | | USDA 123 vs. USDA 138 | | |
|---|---|---|---|---|---|---|---|---|---|
| | USDA 123 | USDA 110 | Other | USDA 123 | USDA 122 | Other | USDA 123 | USDA 138 | Other |
| | % | | | | | | | | |

TABLE IV-continued

Strains recovered from the nodules of PI 371607, PI 377578, and Williams in three nodulation competition treatments established by preinoculation of Monmouth soil with strain USDA 123 followed by inoculation with either strains USDA 110, USDA 122, or USDA 138 at planting (Exp. 3)

| Soybean genotype | USDA 123 vs. USDA 110 | | | USDA 123 vs. USDA 122 | | | USDA 123 vs. USDA 138 | | |
|---|---|---|---|---|---|---|---|---|---|
| | USDA 123 | USDA 110 | Other | USDA 123 | USDA 122 | Other | USDA 123 | USDA 138 | Other |
| PI 371607 | 0b | 100a | 2a | 7b | 98a | 0a | 7b | 97a | 0a |
| PI 377578 | 0b | 98a | 6a | 2b | 97a | 0a | 8b | 97a | 0a |
| Williams | 83a | 25b | 2a | 82a | 44b | 0a | 76a | 44b | 0a |

Values of each genotype-treatment combination are the mean of 60 nodules (15 per replication) taken from the roots of a total of eight plants (two per replication). The total of USDA 123 and the corresponding competitor strain may be greater than 100% because of doubly occupied nodules.

Values within a column not followed by the same letter differ significantly at the 0.05 probability level as tested by Duncan's new multiple range test.

Experiment 4. In an attempt to quantify the effects of restricted nodulation by strain USDA 123 on nodulation and N accumulation when grown in soil, PI 371607, PI 377578, Williams soybean were grown in *B. japonicum*-free soil. When uninoculated, top plant weight and N accumulation in the PI genotypes and Williams were not significantly different (Table V). In soil preinoculated with USDA 123, the nodulation, plant weight, and N accumulation of Williams significantly exceeded that of the PI genotypes. In the case of preinoculation with strain USDA 110, no statistical differences were detected between Williams and the two PI genotypes for nodulation, plant weight, or N content. When treatment consisted of planting in soil preinoculated with strain USDA 123 followed by inoculation with strain USDA 110 at planting, nodule mass was similar in the three genotypes. In this treatment, top dry weight (but not N accumulation) was significantly greater in PI 377578 than in cultivar Williams. The percentage of nodules occupied by strains USDA 123 and USDA 110 was nearly identical to that observed in Exp. 3 despite a difference greater than 100-fold in the amount of inoculant strain applied. Less than 10% of the nodules of PI 371607 and PI 377578 were occupied by strain USDA 123, whereas this strain was present in nearly 80% of the nodules of Williams soybean. Similar to the findings in Exp. 3, strain USDA 110 was present in at least 97% of the nodules formed by the PI genotypes and only 45% of those formed by Williams.

EXAMPLE 2

Several field isolates of *B. japonicum* serogroup 123 were compared with strain USDA 123 for their ability to nodulate two strain USDA 123 restricting soybean genotypes and the production cultivar Williams, and the competitiveness of certain of these isolates was compared with that of an inoculant quality strain on the strain USDA 123 restricting genotype and cultivar Williams.

TABLE V

Nodulation, top dry weight, N accumulation, and bradyrhizobia strains recovered from the nodules of PI 371607, PI 377578, and Williams grown in Monmouth soil and inoculated as indicated (Exp. 4)

| Inoculation treatment and soybean genotype | Nodule dry wt | Top dry wt | Nitrogen accumulation | B. japonicum recovered from nodules | |
|---|---|---|---|---|---|
| | | | | USDA 123 | USDA 110 |
| | mg plant$^{-1}$ | g plant$^{-1}$ | mg plant$^{-1}$ | % | |
| Uninoculated | | | | | |
| PI 371607 | 0a§ | 1.98a | 24a | — | — |
| PI 377578 | 6a | 2.20a | 28a | 0 | 0 |
| Williams | 6a | 1.98a | 31a | 0 | 0 |
| Soil preinoculated with USDA 123 | | | | | |
| PI 371607 | 22b | 2.02b | 29b | — | — |
| PI 377578 | 37b | 2.18b | 30b | — | — |
| Williams | 211a | 3.02a | 66a | — | — |
| Soil preinoculated with USDA 110 | | | | | |
| PI 371607 | 156a | 3.32a | 107a | — | — |
| PI 377578 | 180a | 3.36a | 106a | — | — |
| Williams | 138a | 2.95a | 98a | — | — |
| Soil preinoculated with USDA 123 and inoculated with liquid USDA 110 at planting | | | | | |
| PI 371607 | 211a | 3.18ab | 85a | 6b | 99a |
| PI 377578 | 226a | 3.84a | 95a | 9b | 97a |

TABLE V-continued

Nodulation, top dry weight, N accumulation, and bradyrhizobia strains recovered from the nodules of PI 371607, PI 377578, and Williams grown in Monmouth soil and inoculated as indicated (Exp. 4)

| Inoculation treatment and soybean genotype | Nodule dry wt | Top dry wt | Nitrogen accumulation | B. japonicum recovered from nodules | |
|---|---|---|---|---|---|
| | | | | USDA 123 | USDA 110 |
| Williams | 184a | 3.12b | 81a | 79a | 45b |

Values are the mean of eight plants (two per replication).
Values are the mean of 120 nodules (30 per replication) taken from the roots of a total of eight plants (two per replication). The total of USDA 123 and USDA 110 may be greater than 100% because of doubly occupied nodules.
†Values within a column within an inoculation treatment not followed by the same letter differ significantly at the 0.05 probability level as determined by Duncan's new multiple range test.

MATERIALS AND METHODS

Bacterial strains. All strains of B. japonicum used in this study are listed in Table VI. Those strains whose prefix is a state postal abbreviation were isolated from soybean nodules in those states as described in H. H. Keyser et al. [Appl. Environ. Microbiol. 47: 613–615 (1984)] with the exceptions of IA3H2-6, IA3H2-8, and IA3H2-17, which were kindly provided by Dr. T. E. Loynachan of Iowa State University. Strains USDA 162, USDA 185 and USDA 228 were isolated in our laboratory from soybean root nodules collected in Harbin, Shenyang and Yentai, respectively, People's Republic of China, in 1980. All the above strains were examined for purity by inspection of single colony isolates on agar media and were verified as members of serogroup 123 by reaction with fluorescent antibodies (FAs) prepared against strain USDA 123. These isolates were also examined for cross reaction with FAs prepared against USDA 127 and USDA 129, and with cross-adsorbed FAs prepared against USDA 123, USDA 127 and USDA 129, as described by E. L. Schmidt et al. [Appl. Environ, Microbiol. 51: 1212–1215 (1986)]. These 20 isolates of serogroup 123 were chosen for study on the basis of their diverse geographic origin: 17 isolates from 10 states in the U.S. are included (isolates from the same state are from different locations) and 3 isolates from the P.R.C. Strains USDA 6, USDA 110 and USDA 136 are very effective, "inoculant-quality" strains. They belong to serogroups 6, 110 and 122, respectively. All cultures were maintained on yeast extract-mannitol agar slants.

Soybean genotypes. The production cultivar Williams was initially obtained from Dr. R. Bernard, USDA-ARS, University of Illinois, Urbana, Ill. Genotypes PI 371607 and 377578 were initially obtained from Dr. E. E. Hartwig, USDA-ARS, P. O. Box 196, Stoneville, Mich. These genotypes were increased at Beltsville during 1984. Williams is an improved genotype of known pedigree, and PI 371607 and PI 377578 are unimproved soybean germplasm collected in The People's Republic of China and Thailand, respectively.

Determination of restricted nodulation (Exp. 1). A trail was performed to evaluate the diversity among several members of serogroup 123 for restricted nodulation phenotype on two USDA 123-restricting genotypes. A randomized complete block experimental design was used that consisted of a split plot arrangement of treatments with four replications. Whole plots (pots) were strain inoculation treatments and subplots were soybean genotypes. Monmouth fine sandy loam soil (2.4 Kg per pot) was mixed with dolomite at the rate of 1 g/100 g soil to adjust the pH to 6.5, and received per Kg of soil 5 mMoles $K_2HPO_4$, 2 mMoles $K_2SO_4$, 0.15 mMoles $ZnSO_4$ and 1 uMole $Na_2MoO_4$. This soil had no detectable B. japonicum (10 cells per gram soil) as determined by a most probable number (MPN) test using the plant infection method. Each 17.5 cm plastic pot was planted with 2 seeds each of PI 371607, PI 377578 and Williams, which had been surface sterilized by immersion in acidified $HgCl_2$. Strain inoculation treatments were then applied at the rate of 0.5 ml per seed of a stationary broth culture (approximately $10^9$ cells per ml). Treatments included the 20 isolates of serogroup 123, USDA 123, an uninoculated control, and an equal volume mixture of the effective stains USDA 6, USDA 110, and USDA 136. After covering the seed, 1 cm layer of sterile gravel was placed upon the soil surface. Plants were grown in a greenhouse with natural sunlight supplemented by incandescent light to extend the photoperiod to 18 h. Day and night temperatures were maintained at $25\pm5°$ C. Plants were thinned 3 d after emergence to one seedling of each genotype per pot. At 35 d after planting the plants were removed, the root systems carefully washed, and all nodules were removed for determination of dry weight (after 2 d at 70° C.).

Determination of competitive ability (Exp. 2). An experiment was performed to evaluate the competitive abilities of selected isolates of serogroup 123 on the three soybean genotypes. The experimental design, replication, soybean genotypes, soil and plant growing conditions are as described above. However, in this experiment each pot was thinned to one plant each of the two PI's and two plants each of Williams. Also, as the amount of this particular soil lot was limited, it was extended in this experiment by mixing it with an equal volume of sterile perlite. This mixture contained 1.5 Kg soil in each 17.5 cm pot. From the results of Exp. 1, 6 isolates of serogroup 123 were chosen: SD6-1c and MN6-1b (restricted nodulation on the two PI's), SC2-3c and IA3H2-8 (medium nodulation on the two PI's), and AK1-3a and MN1-1c (high nodulation on the two PI's). Each strain was thoroughly mixed into the soil prior to planting by application of diluted broth inoculum. This was also done with the control strains USDA 110 and USDA 123. MPN counts showed that the population level of the eight strains at planting ranged from 1.07 to $3.83\times10^6$ cells power gram of soil. For USDA 123 and each of the six selected isolates of serogroup 123, eight pots were prepared, for receiving no further treatment and four receiving USDA 110 in a peat preparation at planting. Fine peat, courtesy of Dr. S. Smith, Nitragin Co., Milwaukee, Wis., was autoclaved for 2 h, neutralized with dolomite and mixed with early stationary broth culture of strain USDA 110 to give a final moisture content of 38%. The peat culture was incubated for 2 weeks at 25° C., at which time it was used to coat seed (immediately prior to planting) by rolling seed, covered with a 40% (w/v) suspension of gum arabic, in the peat. This was repeated, resulting in seed completely coated with the peat culture. Peat coated seed of each genotype was sampled at planting to determine the MPN of USDA 110 cells per seed. Results showed that genotypes PI 371607, PI 377578 and Williams carried 5.8, 3.1 and $1.7 \times 10^5$ cells per seed, respectively, at planting. An uninoculated treatment was also included. The plants were grown for 42 days in the greenhouse, at which time they were harvested and the following parameters determined: dry wt of plant tops, total N in plant tops, dry wt of nodules and nodule occupancy in the competition treatments using fluorescent antibodies of USDA 123 and USDA 110. In determining nodule occupancy 30 nodules/treatment/replicate were examined with each FA.

are not discrete groups, but rather are groups separated by convenient break points.

The 20 field isolates of serogroup 123 included members from all 3 known serotypes (123, 127 and 129) of the serogroup (Table VI). Based on reactions using adsorbed FAs, 8 of the isolates belonged to serotype 129, 5 were members of serotype 127, and 4 were members of serotype 123. In addition, 3 isolates (USDA 228, MS6-4a, and KS5-2c) did not react with any of the adsorbed FAs, though they did react with unadsorbed FA 123. Mean nodule mass produced on the two PIs shows that 3 of the 4 serotype 123 isolates (in addition to strain USDA 123) were in the low nodulation class. The other 123 serotype member, MN5-4a, was grouped at the low end of the medium nodulation class. All the isolates of serotype 127 and 129 were in the medium and high classes.

TABLE VI

| | | Nodulation of three genotypes of soybean by 20 isolates of *B. japonicum* serogroup 123 | | | | |
|---|---|---|---|---|---|---|
| | | Mean of PI 371607 and PI 377578 and | | Nodule dry weight (mg per plant) | | |
| Strain | Serotype | (nodulation class) | | PI 371607 | PI 377578 | Williams |
| AK1-3a | 129 | 199 A | (H)§ | 214 A | 185 AB | 241 CD |
| MN1-1c | 127 | 191 AB | (H) | 198 AB | 184 AB | 256 CD |
| USDA 228 | NR | 190 AB | (H) | 202 AB | 179 AB | 438 AB |
| USDA 185 | 127 | 178 ABC | (H) | 104 CDE | 253 A | 358 BCD |
| 6 + 110 + 136 | | 172 ABC | | 160 ABC | 184 AB | 245 CD |
| DE3-1a | 127 | 167 ABC | (H) | 154 ABC | 181 AB | 239 D |
| NC3-1a | 129 | 151 A-D | (H) | 108 CDE | 194 AB | 313 BCD |
| MS6-4a | NR | 130 B-E | (M) | 124 BCD | 136 B-E | 337 BCD |
| SC2-3c | 127 | 129 B-E | (M) | 97 C-F | 160 BC | 281 CD |
| AK9-3b | 129 | 123 C-F | (M) | 125 BCD | 122 B-F | 254 CD |
| NJ1-4c | 129 | 119 C-F | (M) | 88 C-F | 149 BCD | 548 A |
| KS6-3b | 129 | 117 C-F | (M) | 145 ABC | 88 C-G | 278 CD |
| IA3H2-8 | 129 | 90 D-F | (M) | 87 C-F | 93 C-G | 346 BCD |
| NJ2-1a | 129 | 79 E-H | (M) | 80 C-G | 78 D-I | 321 BCD |
| MN5-4a | 123 | 76 E-H | (M) | 52 D-G | 99 C-G | 317 BCD |
| IA3H2-17 | 129 | 68 E-H | (M) | 50 D-G | 86 C-H | 386 BC |
| IA3H2-6 | 127 | 60 F-I | (M) | 55 D-G | 66 E-I | 325 BCD |
| USDA 123 | 123 | 40 GHI | (L) | 36 FG | 44 F-I | 295 BCD |
| KS5-2c | NR | 26 HI | (L) | 20 FG | 32 GHI | 269 CD |
| SD6-1c | 123 | 7 I | (L) | 6 G | 7 HI | 334 BCD |
| MN6-1b | 123 | 5 I | (L) | 4 G | 7 HI | 319 BCD |
| USDA 162 | 123 | 3 I | (L) | 1 G | 5 I | 348 BCD |
| Uninoc. | | 1 I | | 0 G | 3 I | 3 E |

Determined using cross-adsorbed FAs (NR = no reaction with adsorbed FAs).
Values within a column not followed by the same letter differ significantly at the 0.05 probability level as tested by Duncan's new multiple range test.
§H = high, M = medium, L = low.

RESULTS

All 20 isolates of serogroup 123 produced abundant nodule mass on Williams soybean, as determined by comparison with a mixture of effective strains (Table VI). However, on the two PI's there was a wide range of nodule mass produced, including several strains whose nodulation was restricted in a manner similar to USDA 123. In general, strains produced the same relative nodule mass on both PI's. Exceptions to this pattern were strains USDA 185, NC3-1a, SC2-3c and NJ1-4c. Given the few exceptions to this pattern, we ranked the isolates by their mean nodule mass on the two PI's (Table VI). From this ranking we assigned relative nodulation classes: high (isolates with nodulation not significantly different from the top ranked strain, AK1-3a), low (isolates with nodulation equal to or less than that of USDA 123), and medium (isolates between the high and low classes). We recognize that these classes Based upon the results of the first experiment, isolates for inclusion in the competition experiment were chosen: SD6-1c and MN6-1b from the low nodulation class, SC2-3c and IA3H2-8 from the medium nodulation class, and AK1-3a and MN1-1c from the high nodulation class. On PI 371607, the inoculant strain USDA 110 significantly increased nodule mass when applied in competition with strains of the low nodulation class SD6-1c or USDA 123 as compared to the mass produced by these strains alone (Table VII). While there was also a positive response with MN6-1b, it was not statistically significant. These isolates gave a similar response with PI 377578. No nodulation differences were detected with the cultivar Williams among the various single strain or competition treatments. In comparison with the first experiment (see Table VI) the isolates classified as low in nodulation (SD6-1c, MN6-1b and USDA 123) produced greater nodule mass. The reason for the difference is not known, though the plants were grown 7 days longer in the latter experiment and were much more vigorous in appearance. We do not attribute the increased mass to nodulation by indigenous bradyrhizobia in the soil. While the uninoculated treatment showed the presence of indigenous bradyrhizobia, tests with FA's of nodules produced by the SD6-1c and MN6-1b treatment showed all the nodules to be of the 123 serogroup, while the nodules of the uninoculated treatment did not react either with FA of USDA 123 or USDA 110.

was apparent with PI 377578, the difference were not statistically significant. By contrast, no response was seen with Williams soybean as none of the isolates were significantly different from each other or strain USDA 110 in influencing total N accumulation.

TABLE VIII

Competition for nodulation with three genotypes of soybeans between USDA 110 and serogroup 123 isolates

| Serogroup 123 isolate | Nodulation class | Percent nodule occupancy | | | | | | | | |
|---|---|---|---|---|---|---|---|---|---|---|
| | | PI 371607 | | | PI 377578 | | | Williams | | |
| | | 110 | 123 isolate | both | 110 | 123 isolate | both | 110 | 123 isolate | both |
| USDA 123 | Low | 85.8 A | 12.3 C | 1.9 A | 78.1 B | 16.8 D | 3.1 A | 4.8 A | 92.6 BC | 1.7 A |
| SD6-1c | Low | 79.8 A | 14.5 C | 4.2 A | 88.2 A | 9.3 D | 2.5 A | 5.1 A | 91.5 C | 2.5 A |
| MN6-1b | Low | 72.1 A | 22.7 C | 3.8 A | 54.5 C | 41.9 C | 3.5 A | 6.1 A | 91.5 C | 1.7 A |
| SC2-3c | Medium | 16.8 BC | 81.5 A | 1.7 A | 10.7 DE | 83.1 B | 4.4 A | 4.0 A | 94.3 ABC | 1.7 A |
| IA3H2-8 | Medium | 33.9 B | 57.7 B | 7.5 A | 13.3 D | 82.5 B | 4.1 A | 0.8 A | 99.2 A | 0.0 A |
| AK1-3a | High | 17.5 BC | 80.8 A | 0.8 A | 0.8 E | 99.2 A | 0.0 A | 1.7 A | 98.3 AB | 0.0 A |
| MN1-1c | High | 10.8 C | 87.3 A | 1.1 A | 8.9 DE | 90.7 AB | 0.4 A | 1.5 A | 96.7 ABC | 0.0 A |

Nodulation class is based on the mean nodule dry weights produced on PI 371607 and PI 377578 (See Table VI).
Values within a column not followed by the same letter differ significantly at the 0.05 probability level as tested by Duncan's new multiple range test.

TABLE VII

Nodulation of three genotypes of soybean by serogroup 123 isolates alone and in competition with USDA 110

| Inoculation treatment | Nodule dry weight (mg per plant) | | |
|---|---|---|---|
| | PI 371607 | PI 377578 | Williams |
| MN1-1c + USDA 110 | 302 A | 217 A | 222 A |
| AK1-3a | 257 AB | 183 AB | 172 A |
| MN1-1c | 250 ABC | 196 AB | 228 A |
| AK1-3a + USDA 110 | 217 BCD | 178 ABC | 196 A |
| MN6-1b + USDA 110 | 207 BCD | 178 ABC | 202 A |
| IA3H2-8 + USDA 110 | 200 BCD | 174 ABC | 213 A |
| IA3H2-8 | 196 BCD | 180 ABC | 230 A |
| SD6-1c + USDA 110 | 191 BCD | 111 B-E | 237 A |
| USDA 123 + USDA 110 | 183 BCD | 110 B-E | 232 A |
| SC2-3c | 182 BCD | 150 A-D | 239 A |
| USDA 110 | 170 BCD | 161 A-C | 174 A |
| SC2-3c + USDA 110 | 163 CD | 111 B-E | 204 A |
| MN6-1b | 159 D | 88 DE | 212 A |
| USDA 123 | 71 E | 63 DE | 248 A |
| SD6-1c | 38 E | 25 E | 241 A |
| Uninoculated | 26 E | 28 E | 18 B |

Values within a column not followed by the same letter differ significantly at the 0.05 probability level as tested by Duncan's new multiple range test.

TABLE IX

Top nitrogen accumulation in three genotypes of soybean inoculated with serogroup 123 isolates alone and in competition with USDA 110

| Inoculation treatment | Nitrogen accumulation (mg per plant) | | |
|---|---|---|---|
| | PI 371607 | PI 377578 | Williams |
| AK1-3a + USDA 110 | 102 A | 82 AB | 90 A |
| USDA 110 | 95 AB | 97 A | 101 A |
| MN6-1b + USDA 110 | 93 AB | 60 B-E | 105 A |
| AK1-3a | 92 ABC | 80 AB | 95 A |
| IA3H2-8 + USDA 110 | 89 ABC | 74 ABC | 89 A |
| SD6-1c + USDA 110 | 85 ABC | 47 C-F | 97 A |
| IA3H2-8 | 85 ABC | 81 AB | 88 A |
| MN1-1c + USDA 110 | 83 ABC | 85 AB | 94 A |
| USDA 123 + USDA 110 | 80 A-D | 47 C-F | 96 A |
| MN1-1c | 80 A-D | 67 BCD | 86 A |
| SC2-3c | 70 BCD | 42 DEF | 98 A |
| SC2-3c + USDA 110 | 63 CDE | 45 DEF | 101 A |
| MN6-1b | 55 DEF | 36 EF | 94 A |
| SD6-1c | 42 EF | 26 F | 96 A |
| USDA 123 | 37 EF | 36 EF | 101 A |
| Uninoculated | 32 F | 27 F | 32 B |

Values within a column not followed by the same letter differ significantly at the 0.05 probability level as tested by Duncan's new multiple range test.

The 6 selected isolates of serogroup 123 and strain USDA 123 were very competitive for nodulation against USDA 110 on Williams soybean (Table VIII). Strain USDA 110 formed less than 7% of the nodules in each case. The marked influence of the host genotype on competition is seen by comparing this with results obtained with PI 371607. Here, the strains in the low nodulation class (USDA 123, SD6-1c and MN 6-1b) were not competitive against strain USDA 110, the latter forming 72 - 85% of the nodules. The serogroup 123 isolates in the medium and high nodulation class were able to successfully compete against the inoculant strain. This same pattern was found in PI 377578, though strain MN6-1b did compete on an almost equal basis with USDA 110, in contrast to the two other low nodulation class isolates which were not competitive with USDA 110.

Table IX shows the plant nitrogen response in Ex. 2. Strain USDA 110 gave a nitrogen response, through increased symbiotic nitrogen fixation, when in competition with the low nodulation isolates (MN6-1b, SD6-1c and USDA 123) on PI 371607. While the same pattern

We claim:

1. A method for controlling root nodulation in soybean plants comprising:
   a) identifying nodulation by undesired Bradyrhizobium japonicum strains indigenous to a predetermined field;
   b) providing a soybean plant genotype characterized in that it has at least one nodulation inhibitor gene which does not have a corresponding nodulation gene in each of the undesired B. japonicum strains; and
   c) administering to the field an effective amount of a desired strain of B. japonicum, characterized by having a nodulation gene corresponding to the nodulation inhibitor gene in said plant, said amount being effective to nodulate or enhance biological nitrogen fixation of said soybean plant; and
   d) growing said plant in the field and concurrently in the presence of said desired strain of B. japonicum whereby root nodulation by undesirable indigenous B. japonicum strains is reduced or eliminated.

* * * * *